(12) United States Patent
Lin et al.

(10) Patent No.: US 10,279,203 B2
(45) Date of Patent: *May 7, 2019

(54) COMPOSITION FOR PREVENTING OR TREATING DENTIN-ASSOCIATED SYMPTOMS OR DISEASES, AND METHOD USING THE SAME

(71) Applicant: Sancastle Worldwide Corporation, Taipei (TW)

(72) Inventors: Chun-Pin Lin, Taipei (TW); Hong-Ping Lin, Taipei (TW); Wei-Yen Yeh, Taipei (TW)

(73) Assignee: Sancastle Worldwide Corporation, Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/868,559

(22) Filed: Jan. 11, 2018

(65) Prior Publication Data
US 2018/0140873 A1    May 24, 2018

Related U.S. Application Data

(63) Continuation of application No. 13/242,866, filed on Sep. 23, 2011, now Pat. No. 9,901,755.

(51) Int. Cl.
| | |
|---|---|
| A61K 6/00 | (2006.01) |
| A61K 6/06 | (2006.01) |
| A61K 8/02 | (2006.01) |
| A61K 8/19 | (2006.01) |
| A61K 8/25 | (2006.01) |
| A61Q 11/00 | (2006.01) |

(52) U.S. Cl.
CPC ............ *A61Q 11/00* (2013.01); *A61K 6/0008* (2013.01); *A61K 6/0017* (2013.01); *A61K 6/0088* (2013.01); *A61K 6/0612* (2013.01); *A61K 6/0668* (2013.01); *A61K 8/0279* (2013.01); *A61K 8/19* (2013.01); *A61K 8/25* (2013.01); *A61K 2800/412* (2013.01); *A61K 2800/413* (2013.01)

(58) Field of Classification Search
None
See application file for complete search history.

(56) References Cited

U.S. PATENT DOCUMENTS

| | | |
|---|---|---|
| 4,645,662 A | 2/1987 | Nakashima et al. |
| 5,215,740 A | 6/1993 | Domke et al. |
| 5,833,954 A | 11/1998 | Chow et al. |
| 5,879,663 A | 3/1999 | Nakabayashi et al. |
| 2002/0022677 A1 | 2/2002 | Teramae et al. |
| 2007/0183984 A1 | 8/2007 | Haas et al. |
| 2011/0268779 A1 | 11/2011 | Canham |

FOREIGN PATENT DOCUMENTS

| | | |
|---|---|---|
| CN | 1213355 A | 4/1999 |
| CN | 1377252 A | 10/2002 |
| CN | 1554607 A | 12/2004 |
| CN | 101410022 A | 4/2009 |
| CN | 101528279 A | 9/2009 |
| DE | 4301945 A1 | 8/1993 |
| GB | 136442 A | 12/1919 |
| GB | 1 598 233 A | 9/1981 |
| JP | S61-36212 A | 2/1986 |
| JP | 2001-170161 A | 6/2001 |
| JP | 2008-520568 A | 6/2008 |
| JP | 5731459 B2 | 6/2015 |
| TW | 1483740 B | 5/2015 |
| WO | 01/10392 A2 | 2/2001 |
| WO | 01/92422 A1 | 12/2001 |
| WO | 02/30380 A1 | 4/2002 |
| WO | 2008/015117 A2 | 2/2008 |
| WO | 2010/054494 A2 | 5/2010 |
| WO | 2010/058218 A1 | 5/2010 |

OTHER PUBLICATIONS

Gray, R. for Mail Online—Science & Tech, "The end of sensitive teeth? Paste treatment mimics tooth enamel to halt pain—and lasts at least 70 days", Jan. 20, 2015, 6 pages.
American Chemical Society. "A potential long-lasting treatment for sensitive teeth", ScienceDaily. ScienceDaily, Jan. 7, 2015. <www.sciencedaily.com/releases/2015/01/150107123130.htm>.
Chiang et al., "A Novel Mesoporous Biomaterial for Treating Dentin Hypersensitivity", J. Dent Res, 89(3), 2010, pp. 236-240.

*Primary Examiner* — Melissa L Fisher
(74) *Attorney, Agent, or Firm* — Mintz Levin Cohn Ferris Glovsky and Popeo, P.C.; Peter F. Corless; Joohee Lee

(57) ABSTRACT

Provided is a formulation for oral teeth, which includes a plurality of calcium ion carriers and a plurality of calcium-containing particulates. The particulates are carried by the calcium ion carriers, such that the formulation can prevent or rapidly treat dentin-associated symptoms or diseases, while providing a prolonged prophylactic or therapeutic effect.

17 Claims, 7 Drawing Sheets

COMPOSITION FOR PREVENTING OR TREATING DENTIN-ASSOCIATED SYMPTOMS OR DISEASES, AND METHOD USING THE SAME

CROSS REFERENCE TO RELATED APPLICATION

The present application is a Continuation Application of U.S. patent application Ser. No. 13/242,866, filed Sep. 23, 2011. The entire contents of those applications are incorporated herein for all purposes by this reference.

BACKGROUND OF THE INVENTION

1. Field of the Invention

The present invention relates to a formulation for use in oral teeth, and more particularly relates to a formulation for propylaxising and treating dentin-associated diseases or symptoms.

2. Description of Associated Art

Dentin, which is also known as "dentine," is a tissue constituting the tooth matrix, and located between dental enamel and dental pulp. Dentin is composed of 70% of inorganic substance, 20% of organic substance and 10% of water. The hardness of dentin is lower than that of dental enamel, but higher than that of cementum. Dentinal tubules throughout the dentin are arranged radially from the surface of the dental pulp towards the dental enamel. The dentinal tubules are wider at the ends near the dental pulp. The closer toward the surface the dentinal tubules with branches therebetween are, the narrower they are.

Common dentin-associated diseases or symptoms which cause pain, includes dental caries, tooth wearing, enamel loss and dentin hypersensitivity etc.

Dentin hypersensitivity is sometimes referred to as "tooth hypersensitivity" and "hypersensitive dentine." Currently, various types of products or methods for relieving dentin hypersensitivity have been developed. However, up to now, none of the products or methods can provide rapid and long-term relieving effect.

Generally, the clinical methods for treating dentin hypersensitivity can fall into the following two categories: (1) chemical desensitizing method; and (2) physical desensitizing method.

As to the chemical desensitizing methods, corticosteroids were used in the early years to suppress inflammation. However, such methods are ineffective. Further, protein precipitation, which is also categorized as a chemical desensitizing method, utilizes a chemical agent to coagulate and denature the proteins in the dentinal tubule. For example, a formulation containing silver nitrate, phenol, formaldehyde or strontium chloride is used to denature collagen, and then forms precipitates which block the openings of the dentinal tubules. However, such formulation stimulates dental pulp and gingival, and the relapse rate is extremely high. Further, silver nitrate dyes teeth black permanently.

Moreover, chemical desensitizing methods also include a treating method for paralyzing pulp nerves. For example, some commercially available desensitizing toothpastes use potassium nitrate to suppress the excitation of pulp nerves. However, the clinical cases have shown that the pain on a patient cannot be relieved until the desensitizing toothpaste is persistently used for two weeks, and the therapeutic effect can last for only several months. That is to say, the methods for paralyzing pulp nerves cannot provide rapid and long-term therapeutic effects. Also, the long-term use of potassium nitrate leads to disorders associated to the paralysis of pulp nerves.

On the other hand, as to the physical desensitizing methods, for example, a sealant for dentinal tubules is used to directly seal the openings of dentinal tubules. The sealant includes, for example, resins, glass ionomer cements and or the like. For example, Jensen et al. ("A comparative study of two clinical techniques for treatment of root surface hypersensitivity," Gen. Dent. 35:128-132.) proposed a method for directly sealing the openings of dentinal tubules using a resin-type dentin bonding agent. Although this method can immediately relive the pain caused by dentin hypersensitivity, it cannot provide long-term therapeutic effects. More specifically, the clinical cases have shown that, after a 6-months treatment, the resin-type bonding agent detaches significantly from the surfaces of teeth. As to the glass ionomer cements, Low et al. ("The treatment of hypersensitive cervical abrasion cavities using ASAP cement," J. Oral Rehabil. 8(1):81-9) used glass ionomer cements to treat dentin hypersensitivity in 1981. Although glass ionomer cements can provide therapeutic effects, this type of material will be removed by constantly brushing the tooth. Further, Hansen et al. ("Dentin hypersensitivity treated with a fluoride-containing varnish or a light-curd glass ionomer liner," Scand. J. Dent. Res. 100(6):305-9) used resin-enhanced glass ionomer cements to treat dentin hypersensitivity, but still no long-term therapeutic effects were achieved.

Accordingly, it is an urgent and important issue to provide rapid and prolonged effects to relieve dentin-associated symptoms and diseases.

SUMMARY OF THE INVENTION

In view of the foregoing, the present invention provides a formulation for oral teeth, comprising a plurality of calcium ion carriers and a plurality of calcium-containing particulates, wherein the calcium-containing particulates are carried by the calcium ion carriers. Therefore, the formulation for oral teeth of the present invention can prevent or rapidly treat dentin-associated symptoms or diseases, and can provide prolonged prophylactic or therapeutic effects.

The present invention further provides a method for preventing or treating a dentin-associated symptom or disease, comprising a step of administering the aforesaid formulation for oral teeth of the present invention to the oral cavity of a subject.

The present invention further provides a method for dental therapy, comprising the steps of: providing a composition comprising calcium-containing particulates, calcium- and phosphorus-containing particulates, fluoro-containing particulates or a combination thereof and microparticles; mixing the composition and an acidic solution to form a formulation; and administering the formulation to the oral cavity of a subject.

The present invention further provides a composition for oral care, comprising a plurality of microparticles, wherein each of the microparticles has a plurality of pores, and the pores have a pore diameter ranging from 1 to 100 nm; and a calcium-containing component, a phosphorus-containing component, a calcium- and phosphorus-containing component, a fluoro-containing or a combination thereof. Thereby, the composition for oral care of the present invention is beneficial to the prevention or rapid treatment of a dentin-associated symptom or disease, and can provide prolonged prophylactic or therapeutic effects.

Moreover, the present invention provides a method for preventing or treating a dentin-associated symptom or disease, comprising the step of administering the aforesaid formulation for oral care the present invention to the oral cavity of a subject.

In addition, the present invention provides a product comprising the aforesaid formulation for oral care of the present invention. The product comprises dental products, toothpastes, tooth powder, ointments, chewing gums, troches, mouthwash, toothbrushes or strips.

BRIEF DESCRIPTION OF THE DRAWINGS

The present invention can be more fully understood by reading the following detailed description of the preferred embodiments, with reference made to the accompanying drawings, wherein.

DETILED DESCRIPTION OF THE PREFERRED EMBODIMENTS

Figure 1:
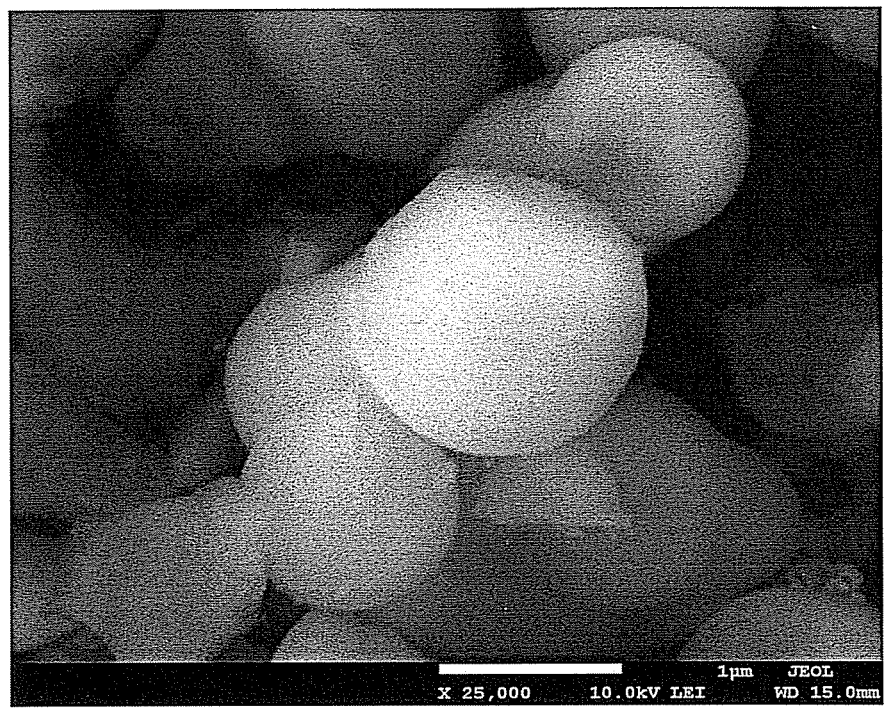
FIG. 1 shows an SEM observation of the Ca—Si-Based porous particles of an embodiment of the present invention.

The following specific examples are used to exemplify the present invention. A person of ordinary skills in the art can conceive the other advantages of the present invention, based on the disclosure of the specification of the present invention. The present invention can also be implemented or applied as described in different specific examples. It is possible to modify and or alter the above examples for carrying out this invention without contravening its spirit and scope, for different aspects and applications.

In order to solve the issues in prior art, the inventors the present invention accomplished a formulation for oral teeth after performing a variety of experiments. The formulation comprises a calcium ion carrier and a calcium-containing particulate, wherein the calcium-containing particulate is carried by the calcium ion carrier.

The form the formulation for oral teeth of the present invention presents is not limited. Preferably, the formulation for oral teeth of the present invention exists as a gel, a paste, a slurry, an emulsion or a glue.

The carrier of the calcium ion of the present invention is not limited, but it may be composed of an organic substance or an inorganic substance. More specifically, in some preferred embodiments, the organic substance constituting the calcium ion carrier is preferably a polymer, and more preferably a porous polymer. In some preferred embodiments, the organic substance constituting the calcium ion carrier may be ester-based polymer or alkene-based polymer. For example, the preferred ester-based polymers may include acrylic latex or polystyrene, and the preferred alkene-based polymer may include nylon. Further, the calcium ion carrier may be composed of a combination of acrylic latex, polystyrene and nylon.

As to the inorganic substance constituting a calcium ion carrier, in some preferred embodiments, the organic substance includes an oxide. The oxide constituting the calcium ion carrier is not limited, but preferably silicon dioxide, silicoaluminate, titanium dioxide, zinc oxide, aluminum oxide or a combination thereof.

In a preferred embodiment of the formulation for oral teeth of the present invention, the calcium ion carrier is a microparticle having a plurality of pores. More specifically, the way the calcium ion carriers carries the calcium-containing particulate is not limited. Preferably, the calcium-containing particulate is adhered to the pores of the microparticles.

The calcium-containing particulate of the present invention is not limited, but preferably composed of calcium oxide, calcium chloride, calcium carbonate, calcium nitrate, calcium hydroxide, calcium salt or a combination thereof. In some preferred embodiments, the calcium-containing particulate may further comprise phosphorus. More specifically, the calcium-containing particulate comprising phosphorus is not limited, but preferably composed of calcium phosphate, hydroxyapatite, tricalcium phosphate, tetracalcium phosphate, $CaHPO_4$, $Ca_8H_2(PO_4)_6\cdot 5H_2O$, $Ca_2P_2O_7$, $Na_2O$—$CaO$—$SiO_2$—$P_2O_5$ or a combination thereof.

In a preferred embodiment of the formulation for oral teeth of the present invention, the pH value of the formulation is in a range of 2 to 10, and preferably in a range of 7 to 10.

The aforesaid components of the formulation of the present invention are only used to exemplary illustrate the proffered embodiment of the present invention, and not intended to limit the scope of the present invention. That is, the formulation for oral teeth of the present invention may further comprise a calcium-ion release agent, which releases calcium ions from the calcium-containing particulates carried on the calcium-ion carries. More specifically, the calcium-ion release agent may be an acidic solution, and preferably at least one selected from the group consisting of phosphoric acid, oxalic acid and citric acid, and more preferably phosphoric acid. The acidic solution may also be an organic acid or inorganic acid related or similar to any one of phosphoric cid, oxalic acid and citric acid.

In a preferred embodiment of the formulation for oral teeth of the present invention, the concentration of the phosphoric acid is in a range of 1% to 65%, preferably in a range of 25% to 45%, and more preferably in a range of 31% to 40%.

In another preferred embodiment of the formulation for oral teeth of the present invention, when the calcium-ion release agent is an acidic solution, the ratio of the contents of the acidic solution and the calcium ion carriers carrying calcium-containing particulates is in a range of 1 to 10 mL/g, preferably in a range of 2 to 5 mL/g.

As described above, the formulation for oral teeth of the present invention may optionally comprise or not comprise an acidic solution, which has a pH value in a range of 2 to 10. In an embodiment, the pH value may be in a range of 7 to 10. Alternatively, in the case of comprising the acidic solution, the pH value of the formulation may be in a range of 4 to 7, preferably in a range of 5 to 6.

Moreover, the formulation for oral teeth of the present invention may further comprise components other than those mentioned above. More specifically, the formulation may further comprise a fluoro-containing component, which may be a fluoro-containing compound, such as a fluoride salt. Preferably, the fluoro-containing component is carried by the aforesaid calcium ion carrier. In some preferred embodiments, the fluoro-containing component is one selected from the group consisting of ammonium fluoride, calcium fluoride, sodium fluoride, potassium fluoride, stannous fluoride, aluminum fluoride, sodium monofluorophosphate, sodium hexafluorosilicate and a combination thereof. Further, the formulation for oral teeth of the present invention may further comprise a pH stabilizer.

In another preferred example of the formulation for oral teeth of the present invention, the particulate diameters of the microparticles are in a range of 0.1 μm to 100 μm, and the pore diameters of the pores are in a range of 1 nm to 100 nm. Preferably, the pore diameters of the pores are in a range of 2 nm to 50 nm.

According to another aspect of the present invention, the present invention further provides a method for preventing or treating a dentin-associated symptom or disease, comprising the step of administering the aforesaid formulation of the present invention to the oral cavity of a subject. More specifically, the dentin-associated symptoms which can be prevented or treated by the method of the present invention are not limited, and may include dentin hypersensitivity, crack tooth syndrome, enamel loss, dentin loss, cemento loss and postoperative hypersensitivity. Enamel loss, dentin loss or cemento loss is generally caused by corrosion, abrasion, wearing or cracking to the teeth. Postoperative hypersensitivity generally occurs after dental operations such as teeth bleaching, prosthodontic or restoration.

On the other hand, the disease which can be prevented or treated by the method of the present invention are not limited, preferably dental caries, root caries, tooth fracture, root fracture, cervical abrasion, tooth wearing or dentin-associated pulp disease.

According to another aspect of the present invention, the present invention provides a method for dental therapy, comprising the steps of: providing a composition comprising calcium-containing particulates, calcium- and phosphorus-containing particulates, fluoro-containing particulates or a combination thereof and microparticles; mixing the composition and an acidic solution to form a formulation; and administering the formulation to the oral cavity of a subject.

In a preferred embodiment of the method for dental therapy of the present invention, the microparticles each has a plurality of pores having pore diameters ranging from 1 to 100 nm. Calcium-containing particulates, calcium- and phosphorus-containing particulates, fluoro-containing particulates or a combination thereof are adhered into the plurality of the pores of the microparticles.

In another preferred embodiment of the method for dental therapy of the present invention, the aforesaid acidic solution is at least one selected from the group consisting of a phosphoric acid, oxalic acid and a combination thereof. In this case, the concentration of the phosphoric acid may be in a range of 1% to 65%, preferably in a range of 25 to 45%, and more preferably in a range of 31% to 40%.

In another preferred embodiment of the method, in the step of forming the formulation, the ratio of the contents of the acidic solution and particles adhered with the calcium-containing particulates, the calcium- and phosphorus-containing particulates, the fluoro-containing particulates or a combination thereof is in a range of 1 mL/g to 10 mL/g. Preferably, in the step of forming the formulation, the ratio of the contents of the acidic solution and the calcium-containing particulates, the calcium- and phosphorus-containing particulates, the fluoro-containing particulates or a combination thereof is in a range of 2 mL/g and 5 mL/g. Further, in the step for forming the formulation, the formed formulation is preferably present as a gel, a paste, a slurry, an emulsion or a glue.

In another preferred embodiment, the method for dental therapy the present invention further comprises a step of administering an aqueous solution to the oral cavity of the subject, and the pH value of the aqueous solution is greater than or equal to 7. The aqueous solution administered in the method for dental therapy the present invention is not limited, preferably may be basic water or basic solution prepared in the labor. With regard to the aforesaid basic water, it may be a basic water obtained any source, such as a commercially available basic water, or basic water prepared in the labor. In addition, the aforesaid basic water has a pH preferably greater than 7.

In another preferred embodiment, the method for dental therapy the present invention further comprises the step of administering water to the oral cavity of the subject. Preferably, prior to the administering of the alkaline solution, water is administered to the cavity of the subject. More specifically, the number of times that water is administered to the oral cavity of a subject is not limited, preferably at least twice.

According to another aspect of the present invention, the present invention provides a composition for oral care, comprising a plurality of microparticles, wherein each of the microparticles has a plurality of pores, and the pores have a pore diameter ranging from 1 to 100 nm; and a calcium-containing component, a phosphorus-containing component, a calcium- and phosphorus-containing component, a fluoro-containing component and a combination thereof.

In a preferred embodiment of the composition for oral care of the present invention, the calcium-containing component, the phosphorus-containing component, the calcium- and phosphorus-containing component, the fluoro-containing component and the combination thereof the present invention are adhered into the pores of the microparticles.

The materials constituting the microparticles of the present invention are not limited, preferably may be composed of organic substance, or may be composed of an oxide. For example, the preferred oxide constituting the microparticles includes silicon dioxide, silicoaluminate, titanium dioxide, zinc oxide, aluminum oxide or a combination thereof. More preferably, the microparticles may be composed of silicon dioxide.

As to the microparticles composed of silicon dioxide, the source for providing silicon dioxide is not limited, and may be an organic compound or an inorganic compound containing silicon dioxide. More specifically, the silicon dioxide particles is preferably formed of silicate, water glass or tetraalkoxy silane.

Moreover, the calcium-containing component of the present invention is not limited, preferably may be selected from the group consisting of calcium oxide, calcium chloride, calcium carbonate, calcium nitrate, calcium hydroxide, calcium salt and a combination thereof.

The phosphorus-containing component of the present invention is not limited, preferably may be selected from the group consisting of phosphoric acid, sodium phosphate, phosphate, hydrogen phosphate, dihydrogen phosphate and a combination thereof.

The calcium- and phosphorus-containing component of the present invention is not limited, preferably may be selected from the group consisting of calcium phosphate, hydroxyapatite, tricalcium phosphate, tetracalcium phosphate, $CaHPO_4$, $CaHPO_4 \cdot 2H_2O$, $Ca_8H_2(PO_4)_6 \cdot 5H_2O$, $Ca_2P_2O_7$, $Na_2O$—$CaO$—$SiO_2$—$P_2O_5$ or a combination thereof.

The fluoro-containing component of the present invention is not limited, preferably may be selected from the group consisting of sodium fluoride, fluorides and salts thereof, and more preferably may be sodium fluoride.

Furthermore, the aforesaid components of the present invention are only used for exemplary illustration, and they are not intended to limit the scope of the present invention. That is, the composition of the present invention may further comprise an additional component other than the aforesaid components.

For example, similar to the aforesaid formulation for oral teeth of the present invention, the composition for oral care of the present invention may further comprise a fluoro-containing component. The fluoro-containing component may be a fluoro-containing compound, such as a fluoro salt. Preferably, the fluoro-containing component is selected from the group consisting of ammonium fluoride, calcium fluoride, sodium fluoride, potassium fluoride, stannous fluoride, aluminum fluoride, sodium monofluorophosphate, sodium hexafluorosilicate and a combination thereof. Further, the composition may further comprise a pH stabilizer.

In another preferred embodiment of the composition for oral care of the present invention, the pore diameters of the pores of the microparticles are in a range of 2 nm to 50 nm, and the particle diameters of the microparticles are in a range of 0.1 μm to 100 μm.

In another preferred embodiment of the composition for oral care of the present invention, the pH value of the composition for oral care of the present invention is not limited, and is preferably in a range of 2 to 10, and more preferably in anyone of the ranges of 7 to 10, 4 to 7 or 5 to 6 based on practical needs.

In addition, the method for preparing the composition for oral care of the present invention is not limited. For example, the method for preparing the composition for oral care of the present invention may be manufactured by sequentially using the sol-gel process to form microparticles having a plurality of pores, and using the impregnation process to allow a calcium-containing component, a fluoro-containing component, a calcium- and phosphorus-containing component, a fluoro-containing component or a combination thereof to adhered into the pores of the microparticle.

According to another aspect of the present invention, the present invention further provides a method for preventing or treating a dentin-associated symptom or disease, which comprises a step of administering the aforesaid composition of the present invention to the oral cavity of a subject. More specifically, the dentin-associated symptom which can be prevented or treated by the aforesaid method of administering the composition of the present invention is not limited, preferably dentin hypersensitivity, crack tooth syndrome, enamel loss, dentin loss, cemento loss or postoperative hypersensitivity. On the other hand, the disease which can be prevented or treated by the aforesaid method of administering the composition of the present invention is not limited, preferably dental caries, root caries, tooth fracture, root fracture, cervical abrasion, tooth wearing or dentin-associated pulp disease.

According to another aspect of the present invention, the present invention provides a product comprising the aforesaid composition of the present invention. The product includes a dental product, a toothpaste, a tooth powder, an ointment, a chewing gum, a chewable tablet, a troche, a mouthwash, a toothbrush or a strip. Preferably, the dental product may include a dental cement, a dental bonding agent, a dental porcelain powder, a pulp capping material, a retrograde filling material, a root canal filling material or a composite resin filling material.

Particularly, when a vital pulp therapy is performed, the aforesaid pulp capping materials can be used to perform a direct or indirect capping treatment. Further, the aforesaid retrograde filling material may be used as a refilling material in apicoectomy.

EXAMPLE

Example 1: Synthesis of Porous Microparticles Constituted by Silicon Dioxide

One gram of gelatin was added to 25 g of deionized water, placed in a thermostatically controlled water batch at 40° C., and stirred for about 15 minutes until complete dissolution was achieved, so as to form an aqueous gelatin solution.

Then, 4 g of sodium silicate was dissolved in 100 g of water, placed in a thermostatically controlled water batch at 40° C., and stirred for about 2 minuets, to form an aqueous sodium silicate solution.

On the other hand, about 3.0 mL of 6M sulfuric acid was added to 100 g of water, and thoroughly stirred, to prepare an acidic solution haing a pH value of about 1. The aqueous sodium silicate solution was mixed with the acidic solution, to adjust pH to about 5. Then, sodium silicate is aged for 3 minutes, and the aqueous gelatin solution was added thereto. The mixture was placed in a thermostatically controlled water batch set at 40° C., and stirred for about 2 hours until complete dissolution was achieved.

Subsequently, all of the mixture (containing the stock solution) was poured into a polypropene (PP) hydrothermal bottle, and placed in an incubator set at 100° C. to undergo a hydrothermal reaction for one day. The obtained product was filtered, rinsed with water, and dried, to obtain a porous silicon dioxide material containing gelatin molecules. The organic matters were removed by calcining at 600° C. for 12 hours, to obtain silicon dioxide-based porous microparticles.

Furthermore, the size of the pores of the silicon dioxide material can be controlled by adjusting the pH value of the solution and the number of days of the hydrothermal reaction. Microparticles of different sizes were prepared optionally by altering the source of silicon oxide and the weight ratios of silicon oxide and gelatin molecules.

Example 2: Preparation of Silicon Dioxide-Based Porous Microparticles Containing Calcium Carbonate Zero point zero nine gram of oxalic acid was dissolved in 10 g of de-ionized water, and 0.84 g of silicon carbonate was added thereto to form a first intermediate solution. Then, 10 g of alcohol was added to the first intermediate solution, and stirred, and 0.5 g of the silicon dioxide-based porous microparticles, as synthesized in example 1, was added thereto to form a second intermediate solution.

The aforesaid second intermediate solution was stirred until it dried up, and then placed in an incubator set at 100° C. for a day. Then, the resultant was taken out from the incubator, and placed into a furnace ventilated with air, with a temperature elevated from 200° C. to 400° C., and held at the temperature for 5 hours. Silicon dioxide-based porous microparticles containing silicon carbonate (hereinafter, referred to as "Ca—Si based-porous particles") were obtained. As shown in FIG. 1, the SEM observation of the Ca—Si based-porous particles of the example is provided.

It is noteworthy that the example is only exemplifying the contents of the present invention, not intended to limit the scope of the present invention. In other words, the method of the example can optionally be used in preparing porous microparticles comprising other component, in addition to calcium carbonate. Further, the method for preparing silicon dioxide-based porous microparticles containing calcium phosphate is substantially the same as that of the present example, except that, in the step of preparing the first intermediate solution, calcium carbonate is replaced with calcium phosphate.

Example 3: Preparation of a Formulation Comprising Ca—Si-Based Porous Particle

Eighty-five point seven percent of commercially available phosphoric acid (J.T. BAKER NALYZED, U.S.A.) was diluted to 31% of a phosphoric acid solution. Zero point zero five gram of the Ca—Si-based particles obtained in example 2 was mixed with 0.15 mL of 31% of phosphoric acid solution, to prepare a formulation comprising silicon-dioxide-based porous microparticles containing calcium carbonate (hereinafter referred to as "CaCO3@pore SiO$_2$ formulation").

Comparative Example 1

Seal & Protect® Formulation

A resin-type dentin bonding agent of commercially available Seal & Protect® (Densensitizer, Dentsply DeTrey, Konstanz, Germany) is provided. Seal & Protect® is a light-curing and self-adhesive sealant composed of urethane dimethacrylate resin, polyrnerizable trimethacrylate resins, dipentaerythritol pentaacrylate phosphate and amorphous silicon dioxide.

Test Example 1

Sealing Effect on Dentinal Tubules In Vitro

Twenty premolars and molars, provided with complete crowns having no caries and no fillers, just removed from a human are collected.

An ultrasonic dental scaler (Sonicflex 2000, Kayo Co Biberbach, Germany) is used to remove dental calculus and periodontal tissues from the premolars and molars. Then, the premolars and molars are stocked in 4° C. distilled water, so as to maintain the freshness of the dentin.

Before applying the formulation, the teeth are taken out of the water, and the enamel at the occlusion site is removed in a horizontal direction using a low speed saw (Isomet low speed saw, Buehler, LTD.), and incised at a distance of 1.5 mm along the direction of the neck to obtain a specimen of dentin. Then, a tapered fissure but (1961 tapered fissure but) is used to create a groove on the back of the experimental area of each of the specimens, to guide the direction of future incision of the specimens. Thirty-seven point five percents of phosphoric acid as gel etchant (Kerr Co USA) is used to acid etch the specimens up to 40 seconds. Then, a large amount of distilled water is used to wash the coating layer, and the surfaces of the specimens are blow-dried.

The formulation of Example 3 and Seal & Protect® of Comparative example 1 are used, respectively, by the following approaches, to coat the specimens.

As to CaCO$_3$@porous SiO$_2$ formulation of Example 3, the formulation is coated and pressed tightly on the surfaces of the specimens using a small brush. After 3 minutes, the formulation on the surfaces is rinsed with water. Then, the above step is repeated for three times, wherein alkaline water with pH of 9 is used at the third time to wash the formulation on the surfaces, As to Seal & Protect® of comparative example 1, Seal & Protect® is coated on the surfaces of tooth samples, and allowed it to react for 20 seconds. Then, the tooth samples are blow-dried for 5 seconds, and illuminated for 10 seconds. Subsequently, Seal & Protect® is coated on the surfaces of the tooth samples, blow-dried for 5 seconds, and illuminated for 10 seconds. The coating of Seal & Protect® is completed.

Finally, a field emission scanning electronic microscope (SEM; Field Emission Scanning Electronic Microscope Hitachi S-800, Hitachi Co., Tokyo, Japan) is used to observe the depth of the precipitates in the dentinal tubules in each of the specimens.

Figure 2A:
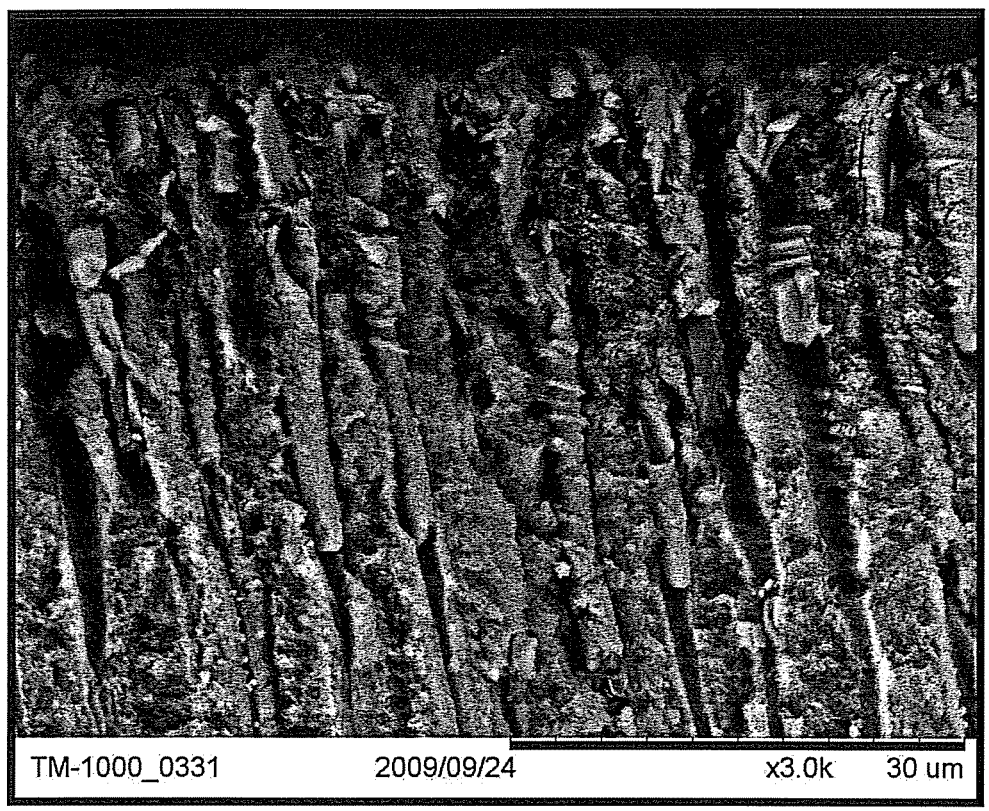
FIG. 2a shows an SEM observation of a dental test slice coated with the $CaCO_3$@porous $SiO_2$ formulation of an embodiment of the present invention.
Figure 2B:
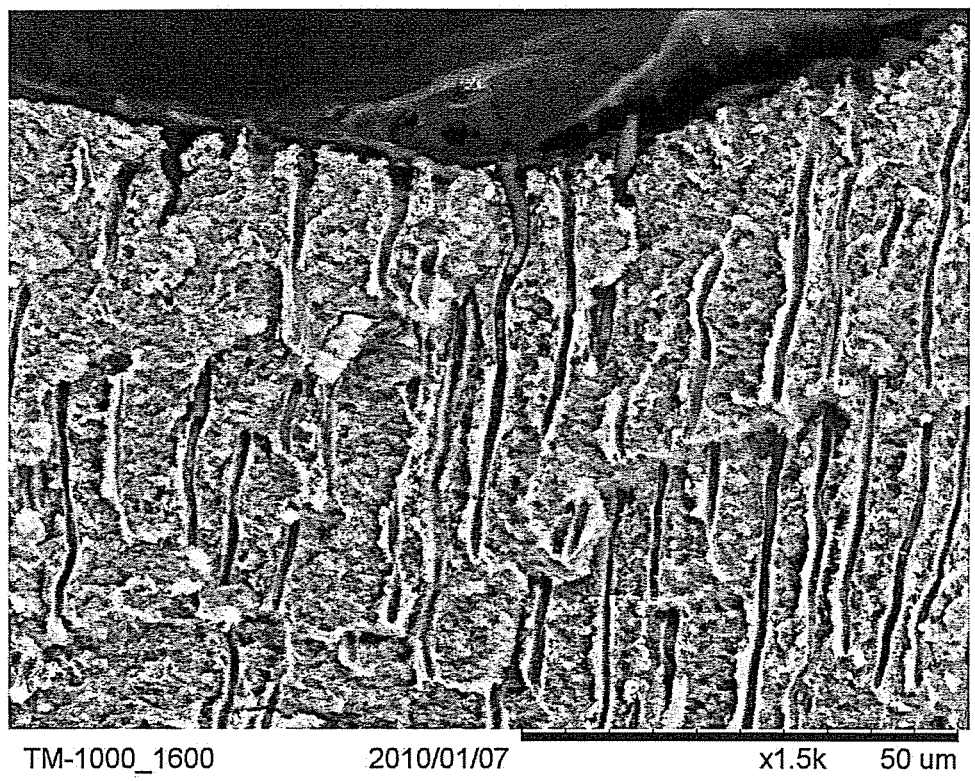
FIG. 2b shows an SEM observation of a dental test slice coated with the Seal & Protect® of a comparative example of the present invention.

FIGS. 2a and 2b show the SEM observations of each of the specimens, respectively. Mores specifically, FIG. 2a shows the SEM observation of dentin specimens coated with CaCO$_3$@porous SiO$_2$ formulation, and FIG. 2b shows the SEM observation of dentin specimens coated with Seal & Protect® formulation.

After comparison, it is found that, in the dentinal tubules, the depths of the precipitates provided by Seal & Protect® of Comparative example are only about 10 μm. There are still existed gaps between the precipitates and the walls of the dentinal tubules, and cannot completely seal the dentinal tubules (please refer to FIG. 2b). However, the depths of the precipitates provided by the formulation of Example 3 are as deep as about 60 μm, and the dentinal tubules are almost 100% sealed. In other words, the CaCO$_3$@porous SiO$_2$ formulation of Example 3 can provide better sealing effect to dentin.

Test Example 2

Permeability Test on Dentinal Tubules In Vitro

The permeability exhibited on the dentin coated with the formulation of example 3 and Seal & Protect® of comparative example, respectively, is evaluated using a flow model test. The lower the determined permeability is, the better the sealing effect of dentin is.

As to the operation of the liquid module test, a glass tube is firstly provided. One end of the glass tube is sealed with a dentin specimen, while the other end of the glass tube is provided with 0.15 g/cm$^2$ of a pressure source. A air bubble is formed in the glass tube. After 72 hours, the distance that the air bubble moves is measured, and the result is used as a baseline. Then, the dentin specimens are coated, while the pressure is continuously provided. After 72 hours, the distance moved that the air bubble moves is measured again, and the result obtained is the permeability distance. The base line and permeability distance are substituted into the following equation, to calculate the permeability of dentin.

Permeability (%)=baseline/permeability distance× 100%

As to the step of coating the dentin specimen, the step is varied according to the coating material.

More specifically, the formulation of Example 3 is coated to the surfaces of the dentin specimens, and then pressed tightly. After 10 minutes, the surfaces of the specimens are rinsed with water.

Seal & Protect® of Comparative example 1 is coated on the surfaces of tooth samples, and allowed them to react for 20 seconds. Then, the tooth samples are blow-dried for 5 seconds, and illuminated for 10 seconds. Next, Seal & Protect® is coated again on the surfaces of the tooth samples. Then, the tooth samples are blow-dried for 5 seconds, and illuminated for 10 seconds. The results showed that the permeability the dentin specimens of Comparative example 1 exhibit are about 40%, whereas the dentin specimens of example 3 are about 15%. That is to say, the formulation of Example 3 of the present invention provided better sealing effect of dentin.

Test Example 3

Sealing Effect on Dentinal Tubules in an Animal Test

Dogs are anesthetized. A cavity with a length of about 5 mm, a width of about 3 mm, and a depth of about 1.5 mm to 2 mm is created on the upper and lower canine on both sides and the neck portion near the first molar of the dog, using a high-speed hand piece equipped with a spray nozzle for dental use. Then, 37.5% of phosphoric acid gel etchant for dental use (Kerr Co. CA, USA) is used for acid etching for 40 seconds, to remove the coating layers. Then, a large amount of water is used to wash the gel etchant away from the surfaces of the teeth, so as to form tooth samples to be filled.

The formulations of Example 3 and Comparative example 1 are used, respectively, to fill the tooth samples by the following approaches.

As to the formulation of Example 3, the formulation is coated and pressed tightly on the surfaces of the tooth samples with dentin exposed from the cavity. After 3 minutes, the coated tooth samples are swabbed using a cotton ball dipped in distilled water. Then, the aforesaid swabbing step is repeated for three times, wherein swabbing is performed using a cotton ball dipped with alkaline water at pH 9 in the third time. Then, a self-polymeric glass ionomer (GC Fuji II™, GC, Tokyo, Japan) is used to fill the cavity.

Seal & Protect® of Comparative example 1 is coated on the surfaces of the tooth samples, and allowed to react for 20 seconds. Then, the samples are blow-dried for 5 seconds, and illuminated for 10 seconds. Seal & Protect® is coated again on the surfaces of the tooth samples. Then, the tooth samples are blow-dried for 5 seconds, and illuminated for 10 seconds. After the completion of the coating of Seal & Protect®, the self-polymeric glass ionomer (GC FujiII™, GC, Tokyo, Japan) is used to fill the cavity.

After 1 week, the tooth samples from each of the groups are removed. Then, the tooth samples are incised to prepare specimens. The depths of the precipitates in the dentinal tubules in the specimens of each of the groups are observed using a field emission scanning electronic microscope (Hitachi S-800, Hitachi Co., Tokyo, Japan).

Figure 3A:
FIG. 3a shows an SEM observation of a dental test slice of a live dog coated with the $CaCO_3$@porous $SiO_2$ formulation of an embodiment of the present invention.
Figure 3B:
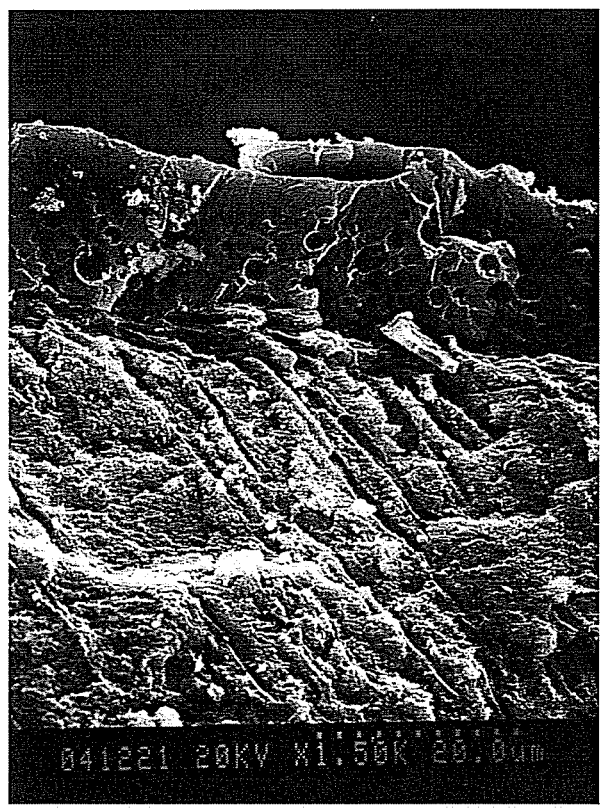
FIG. 3b shows an SEM observation of a dental test slice of a live dog coated with the Seal & Protect® of a comparative example of the present invention.

FIGS. 3a and 3b show the observations of specimens of each of the groups. FIG. 3a shows the SEM observation of the dentin samples of a live dog coated with the $CaCO_3$@porous $SiO_2$ formulation of Example 3, and FIG. 3b shows the SEM observation of the dentin samples of a live dog coated with Seal & Protect® of Comparative example 1.

After comparison, it is found that, in the dentinal tubules, Seal & Protect® of Comparative example 1 coated a resin layer on the dentin surfaces, and the resin layer does not attach tightly with the dentin surfaces. The depth of the resin extending into the dentinal tubules is only about 5 μm (please refer to FIG. 3b). The formulation of Example 3 provides precipitates with depths of about 40 μm, and the dentinal tubules are almost completely sealed (please refer to FIG. 3a). In other words, the $CaCO_3$@porous $SiO_2$ formulation of example 3 can provide better sealing effect to dentin.

Test Example 4

Evaluation of Pulp Irritation

Pulp irritation is evaluated in conformity to the ISO-7405 pulp irritation test.

Firstly, dogs are anesthetized. A cavity with a length of about 5 mm, a width of about 3 mm, and a depth of about 1.5 mm to 2 mm is created on the upper and lower canine on both sides and the neck portion near the first molar of the dog, using a high-speed hand piece equipped with a spray nozzle for dental use. Then, 37.5% of phosphoric acid gel etchant for dental use (Kerr Co. CA, USA) is used for acid etching for 40 seconds, to remove the coating layers. Then, a large amount of water is used to wash the gel etchant away from the surfaces of the teeth, so as to form tooth samples to be filled.

The formulations of Example 3 and comparative example 1 are used, respectively, to fill the tooth samples by the following approaches.

As to the formulation of Example 3, the formulation is coated and pressed tightly on the surfaces of the tooth samples with dentin exposed from the cavity. After 3 minutes, the coated tooth samples are swabbed using a cotton ball dipped in distilled water. Then, the aforesaid swabbing step is repeated for three times, wherein swabbing is performed using a cotton ball dipped with alkaline water at pH=9 in the third time. Then, a polymeric glass ionomer (GC Fuji II™, GC, Tokyo, Japan) is used to fill the cavity.

Seal & Protect® of Comparative example 1 is coated on the surfaces of the tooth samples, and allowed them to react for 20 seconds. Then, the samples are blow-dried for 5 seconds, and illuminated for 10 seconds. Seal & Protect® is coated again on the surfaces of the tooth samples. Then, the tooth samples are blow-dried for 5 seconds, and illuminated for 10 seconds. After the completion of the coating of Seal & Protect®, a self-polymeric glass ionomer (GC FujiII™, GC, Tokyo, Japan) is used to fill the cavity.

On days 7, 28 and 70, the tooth samples of each of the groups to be filled is incised to be made into test slices for pulp irritation, in conformity to ISO-7405 pulp irritation test. Then, an optical microscope is used to observe the levels of inflammation of the cells in the pulp cavity of the slices of each of the groups.

Figure 4A:
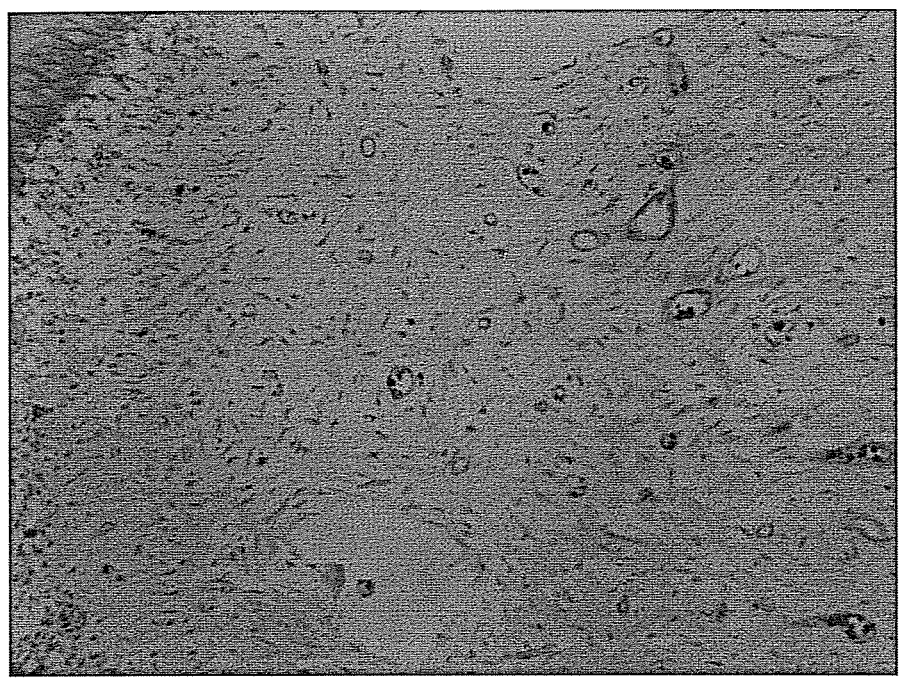
FIG. 4a shows an observation of the pulp tissue morphology of a dental test slice of a live dog coated with the $CaCO_3$@porous $SiO_2$ formulation of an embodiment of the present invention.
Figure 4B:
FIG. 4b shows an observation of the pulp tissue morphology of a dental test slice of a live dog coated with the Seal & Protect® of a comparative example of the present invention.

FIG. 4a and FIG. 4b show the observations of the levels of inflammation of the cells in the pulp cavity of the slices of each of the groups on day 7. More specifically, FIG. 4a shows the observation of the pulp tissue morphology of the dentin specimens of a live dog coated with the CaCO₂@porous SiO₂ formulation of Example 3, and FIG. 4b shows the observation of the pulp tissue morphology of the dentin specimens of a live dog coated with Seal & Protect® of comparative Example 1.

As shown in FIG. 4b, moderate inflammation is observed in the test slices filled with Seal & Protect® of Comparative example 1. More specifically, it is observed that the cell densities in the pulp tissues are elevated, lymphocytes are infiltrated, and the blood vessels are filled with red blood cells.

By contrast, as shown in FIG. 4a, the test slices filled with the CaCO₃@porous SiO₂ formulation of Example 3 showed no inflammation or mild inflammation. More specifically, the pulp tissues had the same morphology as that of the normal pulp tissues. There are no inflamed cells, or scarce inflamed cells. No angiogenesis or diapiresis are observed in the pulp tissues.

It is known from the results of test example 3 that, the CaCO₃@porous SiO₂ formulation of Example 3 provided stronger anti-inflammation ability for a long period. Thus, the CaCO₃@porous SiO₂ formulation of example 3 can provide a therapeutic effect at long-term.

The invention has been described using exemplary preferred embodiments. However, it is to be understood that the scope of the invention is not limited to the disclosed embodiments. On the contrary, it is intended to cover various modifications and similar rearrangement. The scope of the claims therefore should be accorded the broadest interpretation so as to encompass all such modifications and similar arrangements.

What is claimed is:

1. A method for treating a dentin-associated symptom or disease in a subject in need thereof, comprising administering a formulation to an oral cavity of the subject, wherein the formulation comprises:
    a plurality of calcium ion carriers which are silicon dioxide microparticles having a plurality of pores;
    a plurality of calcium-containing particulates composed of calcium carbonate wherein the calcium-containing particulates are carried by the calcium ion carriers and adhered into the plurality of pores of the microparticles; and
    an acidic solution for releasing calcium ions from the calcium-containing particulates carried by the calcium ion carriers for forming precipitation deep in dentinal tubules,
    wherein the silicon dioxide microparticles have particle diameters in a range of from 0.1 μm to 100 μm, the plurality of pores have pore diameters in a range of from 1 nm to 100 nm, and the formulation has a pH value in a range of from 2 to 6.

2. The method of claim 1, wherein the dentin-associated symptom comprises dentin hypersensitivity, crack tooth syndrome, enamel loss, dentin loss, cemento loss, or post-operative hypersensitivity.

3. The method of claim 1, wherein the dentin-associated disease comprises dental caries, root caries, tooth fracture, root fracture, cervical abrasion, tooth wearing, or dentin-associated pulp disease.

4. The method of claim 1, wherein the pore diameters of the plurality of pores are in a range of from 2 nm to 50 nm.

5. The method of claim 1, wherein the acidic solution is at least one selected from the group consisting of a phosphoric acid solution, an oxalic acid solution and a citric acid solution.

6. The method of claim 5, wherein the acidic solution is the phosphoric acid solution.

7. The method of claim 6, wherein the phosphoric acid solution has a concentration in a range of from 1% to 65%.

8. The method of claim 7, wherein the concentration of the phosphoric acid solution is in a range of from 25% to 45%.

9. The method of claim 8, wherein the concentration of the phosphoric acid solution is in a range of from 31% to 40%.

10. The method of claim 1, wherein a ratio of the volume of the acidic solution to the weight of the calcium ion carriers carrying the calcium-containing particulates is in a range of from 1 mL/g to 10 mL/g.

11. The method of claim 10, wherein the ratio of the volume of the acidic solution to the weight of the calcium ion carriers carrying the calcium-containing particulates is in a range of from 2 mL/g to 5 mL/g.

12. The method of claim 1, wherein the formulation is present as a gel, a paste, a slurry, an emulsion or a glue.

13. The method of claim 1, wherein the formulation has a pH value in a range of from 4 to 6.

14. The method of claim 1, wherein the formulation has a pH value in a range of from 5 to 6.

15. The method of claim 1, wherein the formulation further comprises at least one of a phosphorus-containing component and a fluorine-containing component.

16. The method of claim 15, wherein the phosphorus-containing component is at least one selected from the group consisting of phosphate, hydrogen phosphate, dihydrogen phosphate, hydroxyapatite, sodium phosphate, calcium phosphate, tricalcium phosphate, tetracalcium phosphate, CaHPO₄, Ca₈H₂(PO₄)₆·5H₂O, Ca₂P₂O₇, Na₂O—CaO—SiO₂—P₂O₅ and any combination thereof.

17. The method of claim 15, wherein the fluorine-containing component is at least one selected from the group consisting of ammonium fluoride, calcium fluoride, sodium fluoride, potassium fluoride, stannous fluoride, aluminum fluoride, sodium monofluorophosphate, sodium hexafluorosilicate and any combination thereof.

* * * * *